United States Patent [19]

Hille et al.

[11] Patent Number: 5,705,186
[45] Date of Patent: Jan. 6, 1998

[54] PHARMACEUTICAL COMPOSITION FOR THE SYSTEMIC TRANSDERMAL ADMINISTRATION HAVING THE ACTIVE SUBSTANCE MORPHINE-6-GLUCURONIDE

[75] Inventors: Thomas Hille, Neuwied; Karlheinz Otto, Bad Aibling, both of Germany

[73] Assignee: Lts Lohmann Therapie-Systeme GmbH, Neuwied, Germany

[21] Appl. No.: 693,338

[22] PCT Filed: Jan. 5, 1995

[86] PCT No.: PCT/EP95/00031

§ 371 Date: Oct. 9, 1996

§ 102(e) Date: Oct. 9, 1996

[87] PCT Pub. No.: WO95/20966

PCT Pub. Date: Aug. 10, 1995

[30] Foreign Application Priority Data

Feb. 7, 1994 [DE] Germany ............ P 44 03 709.0

[51] Int. Cl.$^6$ .................................................. A61F 13/02
[52] U.S. Cl. ............................................ 424/448; 424/449
[58] Field of Search .................................... 424/448, 449

[56] References Cited

U.S. PATENT DOCUMENTS 3,598,122  8/1971  Zaffaroni ......................... 128/268

FOREIGN PATENT DOCUMENTS

| 3 315 272 | 3/1986 | Germany. |
| 3 843 239 | 2/1990 | Germany. |
| 88/01497 | 3/1988 | WIPO ............... A61F 13/00 |
| 92/08459 | 5/1992 | WIPO ............... A61K 31/485 |
| 93/03051 | 2/1993 | WIPO. |
| 93-05057 | 3/1993 | WIPO. |

OTHER PUBLICATIONS

Oguri, J. Pharmal. Soc. Japan (Yakugaku Zasshi), *100* (2), pp. 117–125 (1980).

Heilmann, Therapeutische Systeme–Konzept und Realisation programmierter Arzneiverabreichung, 4th Edtion, Ferdinand Enke Verlag, Stuttgard, 1984 (page 26).

Franz, The Journal of Investigative Dermatology, vol. 64, pp. 190–195 (1975).

*Primary Examiner*—D. Gabrielle Phelan
*Attorney, Agent, or Firm*—Wenderoth, Lind & Ponack

[57] ABSTRACT

A pharmaceutical composition for systemic transdermal administration containing morphine-6-glucuronide or a pharmaceutically acceptable acid addition salt thereof as the active agent.

3 Claims, No Drawings

PHARMACEUTICAL COMPOSITION FOR THE SYSTEMIC TRANSDERMAL ADMINISTRATION HAVING THE ACTIVE SUBSTANCE MORPHINE-6-GLUCURONIDE

This application is a 371 of PCT/EP95/00031, filed Jan. 5, 1995.

The present invention relates to the systemic transdermal administration of morphine-6-glucuronide.

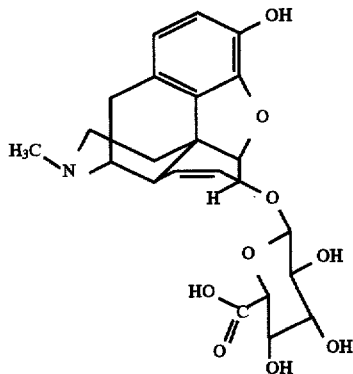

BACKGROUND OF THE INVENTION

Morphine-6-glucuronide (glucuronic acid-6-(7,8-didehydro-4,5 epoxy-17-methylmorphinan-3,6 diolyl) ester) is described in literature as active metabolite of morphine, being more effective than the morphine itself (Oguri, K., J. pharmal. Soc. Japan [Yakugaku Zasshi] 100, 117 (1980)). The synthesis of morphine-6-glucuronide and of the pharmaceutically usable acid addition salts are described in WO-9305057 and WO-9303051.

Morphine is the drug of choice for the treatment of chronic pain, e.g., in patients suffering from a tumor. The administration of the relatively high daily doses involves some difficulties. Although morphine-6-glucuronide has a higher effectiveness its medical application is still in the beginning. Thus, it is the object of the present invention to find a possibility of applying morphine-6-glucuronide in a simple manner and in the required dosage.

DESCRIPTION OF THE INVENTION

Most surprisingly, this object is achieved by administering morphine-6-glucuronide or its salts transdermally. This solution is surprising all the more since—contrary to all expectations—morphine-6-glucuronide diffuses through the skin more easily than the smaller-sized morphine.

This result could not be expected since a glucuronated compound, as compared with the parent compound, has an increased hydrophilia and polarity, involving the fact that the skin is less passable.

Since morphine-6-glucuronide is an active metabolite of morphine it must be assessed like this with respect to toxicology. This is an advantage of morphine-6-glucuronide as compared with other opioids, such as fentanyl and its derivatives.

The term "pharmaceutical composition for the transdermal administration" is meant to comprise any conventional liquid, semiliquid, or solid preparation, e.g., solutions, ointments, pastes, gels, tinctures, and the like, or polymer-containing matrices.

A transdermal therapeutic system (TTS) is meant to be understood according to Zaffaroni as "a drug-containing device or administration form continuously releasing one or several drugs at a predetermined rate over a predetermined period of time to a fixed place of application" (quoted according to: Hellmann, Klaus: Therapeutische Systeme—Konzept und Realisation programmierter Arzneiverabreichung, 4th edition, Ferdinand Enke Verlag, Stuttgart 1984, p. 26). In the present case the place of application is on the skin.

The structure of transdermal systems is known to those skilled in the art. DE 33 15 272, DE 38 43 239, and U.S. Pat. No. 3,598,122 are examples of patent describing the basic structure.

When a transdermal therapeutic system is applied on the skin of a patient, the drug is to be released to take a topic or systemic effect in the patient. Administration forms of this kind have been used therapeutically for some time. The particularly preferred transdermal system in the form of a patch consists of a backing layer which is impermeable to the active substance, a pressure sensitive adhesive reservoir layer, and optionally of a removable protective layer.

In this connection, the backing layer which is impermeable to the active substance may consist of a flexible or inflexible material. Substances suitable for its production are polymeric sheets or foils, such as an aluminum foil, which are used alone or coated with a polymeric substrate. Textile fabrics may also be used, provided that the components of the reservoir, owing to their physical property, cannot penetrate through them. According to a preferred embodiment, the backing layer is a composite of an aluminized foil.

The reservoir layer comprises a polymer matrix and the active substance, the polymer matrix having the property of ensuring the cohesion of the system. It consists of a base polymer and, optionally, of the usual additives. The choice of the base polymer depends on the chemical and physical properties of the active substance. Examples of such polymers include rubber, rubber-like, synthetic homo-, co-, or block polymers, polyacrylic acid esters and their copolymers. In principle, any polymer is suitable that is used in the production of pressure sensitive adhesives, is physiologically acceptable, and which does not decompose morphine-6-glucuronide. Particularly preferred are those consisting of block copolymers based on styrene and 1,3-dienes, polyisobutylenes, or of polymers of acrylate and/or methacrylate. Linear styrene-isoprene-block-copolymers are particularly used of the block copolymers based on styrene and 1,3-dienes.

The preferred polymers based on acrylate are acrylate copolymers of 2-ethyl hexyl acrylate, vinyl acetate, and acrylic acid with or without chelate esters. The preferred methacrylates are copolymers based on dimethylaminoethyl methacrylates and neutral methacrylic acid esters.

The kind of possible additives depends on the polymer used and on the active substance: According to their function they may be classified into plasticizers, tackifiers, stabilizers, carriers, diffusion and penetration regulating additives, and fillers. The physiologically acceptable substances suitable for this purpose are known to the skilled artisan. The self-tackiness of the reservoir layer is strong enough to ensure a permanent contact to the skin. Particularly preferred tackifiers are esters of colophony. Particularly the methyl esters and glycerol esters of colophony are preferably used as esters of hydrogenated colophony.

Examples of suitable plasticizers include diesters of dicarboxylic acid, e.g., di-n-butyladipate, as well as triglycerides, in particular medium-chain triglycerides of the caprylic/capric acid of coconut oil. Additional examples of a suitable plasticizer include isopropyl myristate, dioctyl cyclohexane, and the like.

The removable protective layer which contacts the reservoir layer and is removed prior to application consists, for example, of the same materials as those used for the production of the backing layer, provided that they are rendered removable, e.g., by means of a silicone treatment. Other removable protective layers are, for example, polytetrafluoroethylene, treated paper, cellophane, polyvinyl chloride, and the like. If the laminate according to the present invention is divided into formats corresponding to the respective therapy (patches) prior to application of the protective layer, the formats of the protective layer to be applied then may have a projecting end facilitating their removal from the patch.

The transdermal system according to the present invention is manufactured by homogeneously mixing the active substance together with the components of the pressure sensitive adhesive reservoir layer, optionally in solution, and spreading it onto the backing layer which is impermeable to the active substances, followed by removal of the solvent/s, if necessary. Subsequently, the adhesive layer is provided with a corresponding protective layer.

A preferred acid addition salt is the hydrochloride. Accordingly, morphine-6-glucuronide and its salts are used to manufacture an agent for the systemic transdermal administration to treat intense pain.

The present invention will be illustrated in more detail by means of the following example:

EXAMPLE:

20 g of n-heptane and 80 g of methyl ethyl ketone are mixed. 7.2 g of morphine-6-glucuronide is dissolved in 90 g of this mixture. After complete dissolution of the active substance, 40 g of a linear styrene-isoprene-styrene block polymer and 5.6 g of triglycerides of the caprylic/capric acids of coconut oil ("medium-chain triglycerides", German Pharmacopoeia 10th ed.) are added in portions. Under exclusion of light, stirring is effected at room temperature for 8 hours up to complete dissolution, and the obtained solution is spread on an aluminized and siliconized polyethylene sheet by means of a 250 µm coating knife.

After the solvent has been removed by drying at 50° C. for 25 minutes, the adhesive film is covered with a polyester sheet of 15 µm thickness. An area of 16 cm$^2$ is punched by means of suitable punching tools, and the edges are separated off.

The stability of the active substance in the system was shown by an assay carried out immediately after the completion and after a 3-month storage respectively. Neither the decomposition products, morphine base and glucuronic acid known from literature, nor other ones not yet described could be detected. The following method was used for this purpose:

Preparation of samples:

A patch provided with a cover sheet is divided into four parts by cutting with scissors. The cover sheet is removed and shaken together with the patch portions in a lock-up, light-protected glass vessel containing 50.0 ml of tetrahydrofuran (p.a.) for at least 2 hours. It is then subjected to an ultrasonic treatment for 10 min. and centrifuged, followed by dilution with methanol for HPLC and renewed centrifugation.

Subsequently, the content of the morphine-6-glucuronide in the centrifugate is determined by means of HPLC.

It is decisive for the stability of the active substance that the polymers, resins, and plasticizers used do neither contain free hydroxyl groups nor polyethoxy groups. Otherwise, the portion of active substance which is present in dissolved form would be subject to hydrolysis. For this reason resins and plasticizers belonging to the family of the esters were chosen.

The choice of the solvent or solvent mixture is also decisive for the stability of the active substance, if said solvent or solvent mixture, prior to drying, acts upon the active substance for several hours. The portion of the higher-boiling solvent probably required to suppress bubbling must be as low as possible. In the present example this is achieved by choosing a mixture of butanone and n-heptane which form an azeotropic mixture (ratio of butanone: n-heptane 70:30, boiling point 77° C.; boiling point of butanone: 79.6° C.; boiling point of n-heptane: 98.5° C.). Despite mild drying a maximum residual moisture of less than 0.4% may be achieved thereby.

Using this formulation example, a permeation experiment was carried out in-vitro. For this purpose an in-vitro-standard-test known to the skilled artisan was used. Excised mice skin was used as skin model, physiological saline as acceptor medium, and the diffusion cell according to Franz (Franz, T. J., J. Invest. Dermatol. 64, 194–195, (1975)) was used as apparatus. The formulation is applied on one side of intact skin, while the other side is in contact with physiological saline. The assay in the acceptor medium is effected by means of HPLC. A flux of 2.871 mg/2.54 cm$^2$×24 h was achieved, that of morphine from an analogous system amounting to 1.886 mg/2.54 cm$^2$×24 h.

Excised mice skin is known to those skilled in the art as a model for in-vitro tests. Based on the high value achieved, it may be assumed that morphine-6-glucuronide, also in-vitro, will diffuse through human skin more easily as compared with morphine which does not achieve such a flux.

We claim:

1. In a transdermal therapeutic system in the form of a patch, the patch comprising an impermeable backing layer, a pressure sensitive adhesive polymer matrix reservoir layer, and an optional removable protective layer, the improvement wherein the matrix reservoir layer contains, as an active agent, an effective amount of morphine-6-glucuronide or a pharmaceutically applicable acid addition salt thereof.

2. A system according to claim 1 wherein the active agent is the hydrochloride of morphine-6-glucuronide.

3. A method for the treatment of pain which comprises applying to the skin of a patient in need of such treatment a transdermal therapeutic system as defined in claim 1.

* * * * *